United States Patent [19]

Duran

[11] Patent Number: 5,545,215
[45] Date of Patent: Aug. 13, 1996

[54] EXTERNAL SIGMOID VALVE COMPLEX FRAME AND VALVED CONDUIT SUPPORTED BY THE SAME

[76] Inventor: Carlos G. Duran, Wellington Court 116 Knightsbridge, London SW1, United Kingdom

[21] Appl. No.: 306,202

[22] Filed: Sep. 14, 1994

[51] Int. Cl.$^6$ ..................................................... A61F 2/24
[52] U.S. Cl. ............................................. 623/2; 623/900
[58] Field of Search ........................................ 623/2, 900

[56] References Cited

U.S. PATENT DOCUMENTS

| | | | |
|---|---|---|---|
| 4,218,782 | 8/1980 | Rygg | 623/2 |
| 4,343,048 | 8/1982 | Ross et al. | 623/2 |
| 4,372,743 | 2/1983 | Lane | 8/94.11 |
| 4,451,936 | 6/1984 | Carpentier et al. | 623/2 |
| 4,624,822 | 11/1986 | Arrv et al. | 623/2 |
| 4,692,164 | 9/1987 | Dzemeshkevish et al. | 623/900 |
| 5,139,515 | 8/1992 | Robicsek | 623/2 |
| 5,197,979 | 3/1993 | Quintero et al. | 623/2 |
| 5,376,112 | 12/1994 | Duran | 623/2 |

FOREIGN PATENT DOCUMENTS

| | | | |
|---|---|---|---|
| 515324 | 11/1992 | European Pat. Off. | 623/2 |
| 9014804 | 12/1990 | WIPO | 623/1 |

OTHER PUBLICATIONS

Kirklin, John W. et al. "Intermediate–term Fate of Cryopreserved Allograft and Xenograft Valved Conduits", *Ann Thorac Surg* 44: 598–606, Dec. 1987.

Hawkins, John A. et al. "Midterm results with cryopreserved allograft valved conduits from the right ventricle to the pulmonary arteries", *The Journal of Thoracic and Cardiovascular Surgery*, 104: 910–6, 1992.

Urrea, Miguel S. et al. "Ross Operation Using a Bovine Biopros–tethic Valve with Autologous Pericardial Conduit in the Pulmonary Position", *Texas Heart Institute Journal*, vol. 20, No.4 1993:271–4.

Edward, William D. et al. "Surgical Pathology of Obstructed, Right–Sided, Porcine–Valved Extracardiac Conduits" *Arch Pathol Lab Med*, vol. 107:400–5, Aug. 1983.

Kouchoukos, Nicholas T. et al. "Replacement of the Aortic Root With a Pulmonary Autograft in Children and Young Adults with Aortic–Valve Disease", *The New England Journal of Medicine*, vol. 330, No.1:1–6 Jan. 6, 1994.

Ross, D. et al. "The Pulmonary Autograft—A Permanent Aortic Valve", *Eur J Cardio–thorac Surg* (1992) 6: 113–117.

(List continued on next page.)

*Primary Examiner*—David H. Willse
*Assistant Examiner*—Bruce E. Snow
*Attorney, Agent, or Firm*—Klein & Szekeres

[57] ABSTRACT

A frame to be placed as an external support of a biological valved conduit containing three leaflets. This external frame, made of biocompatible metal or plastic is sutured to the outer surface of the valved conduit made of biological or biocompatible membrane or sigmoid valve root in order to maintain its natural geometry. The frame has a general cylindrical configuration, circular as viewed from above and below. From a side view however, both upper and lower ends of the cylinder present three convex curvatures joined at equidistant points of the circumference. These upper and lower curves are joined by three vertical struts, so that three large saddle shaped paraboloid gaps result. The frame is a wire-like structure that follows perfectly the anatomical shape of the three sinuses of Valsalva, i.e. it corresponds to the external aspect of the line of implantation of the three sigmoid cusps below and the curved line of the sino-tubular junction above. The three vertical struts correspond to the three commissural areas. The frame is designed to be placed on the external surface of a valved conduit or a sigmoid valve root and therefore does not interfere with the natural movements of the three cusps and does not enter in contact with the circulating blood stream. The valved conduit is made of biological or biologically compatible membrane with three bulges corresponding to the three sinuses of Valsalva and three leaflets.

17 Claims, 5 Drawing Sheets

OTHER PUBLICATIONS

Jonas, Ricahrd A. et al. "Long–term follow–up of patients with synthetic right heart conduits", *Congenital Heart Disease*, vol. 72 (suppl II): II–77–II–83, Sep. 1985.

Chiu IS, et al. "Reconstruction of right ventricular outflow tract by autologous pericardial tri–semilunar valve with sinus of Valsalva: report of a case with absent pulmonary valve",*Taiwan–I–Hsueh–Hui–Tsa–Chih;* 1989 Jul.; 88(7); p. 718–21.

Salles, C. A. et al. "Early experience with crimped bovine pericardial conduit for arterial reconstruction", *European Journal of Cardio–thoracic Surgery;* (1991) 5:273–279.

Hikara Matsuda et al. "Hand–Made Valved Conduit with High–Porosity Knitted Graft and Glutaraldehyde–Treated Autologous Pericardial Trileaflet Valve", *Artif Organs,* vol. 14, No. 5 1990; p. 392–394.

EXTERNAL SIGMOID VALVE COMPLEX FRAME AND VALVED CONDUIT SUPPORTED BY THE SAME

BACKGROUND OF THE INVENTION

1. Field of the Invention

The present invention is in the field of heart valve implantation. More particularly, the present invention is directed to a novel external support or frame designed to be affixed on the exterior of a natural sigmoid aortic or pulmonary valve root or a manufactured valved conduit made of biological material. The primary function of the external support frame is to maintain the appropriate geometry of the sigmoid valve complex which includes leaflets and sinuses of Valsalva, particularly at the time of surgical implantation of the complex. The present invention is also directed to the design and process of manufacture of the valved conduit made of biological membranes, in combination with the external support frame.

2. Brief Description of the Prior Art

The outflow tract of the right ventricle of the human heart comprises a muscular part situated in the outlet of the right ventricle, the pulmonary sigmoid valve and the beginning or origin of the pulmonary artery. This tract is often abnormal because of a congenital heart defect, or in some patients with prior cardiac surgery the tract is absent because it has been used in surgery to transfer the pulmonary valve of the patient into the aortic position as an aortic replacement. The just noted surgical operation, also called "switch" or the "Ross Procedure", is becoming increasingly popular since it results in a living valve in the aortic position as is described for example by Ross D. in *Eur. J. Cardiothorac Surg* 1992;6:113. The end result of this operation is that the patient, like the patient having a congenitally underdeveloped outflow tract, suffers from a lack of continuity between the right ventricle and the pulmonary artery. Furthermore, some complex congenital heart malformations are also presently treated by surgically by-passing the hypoplastic right ventricle with a conduit.

In order to bridge the gap between the right ventricle and the pulmonary artery in the above-summarized cases, several solutions have been suggested and used. These include the use of pulmonary or aortic homografts obtained from a cadaver (Hawkins J. A., *J. Thoracic Cardiovasc Surg.* 1992;104:910), heterografts obtained from animals (Edwards W. D., *Arch. Pathol. Lab. Med.* 1983; 107:400), patches of different materials with or without a single cusp, and cylindrical tubes made of different materials including bovine pericardium (Urrea Ms. *Texas Heart J.* 1993; 20:271).

All of the foregoing prior art solutions are laden with problems or serious risks either immediately after their implantation or thereafter. Kinking and partial obstruction of the implanted conduit, after the chest is closed, and lack of pulmonary valve competence (which always occurs with patches) can complicate the early post-operative period. Long term problems of durability are encountered often. These include calcification of the homografts and biopros-thesis, particularly in children (see Kirklin J. W. *Ann. Thorac. Surg.* 1987; 44:598), and progressive stenosis due to peel formation in the Dacron conduits (see Jonas R. A. *Circulation* 1985;72 (Suppl 2):77).

In view of the foregoing, there is a need to develop a new type of valved conduit to be used in the right side of the heart. The present invention represents a significant advance in this direction.

Moreover, human (homologous) and animal (heterologous) aortic and pulmonary valves are still used in the state-of-the-art for transplantation into patients suffering from aortic or pulmonary disease. Initially in the prior art these valves were dissected so that only the three leaflets were left with a small rim of arterial wall and myocardium used for suturing the replacement valve to the patient's own tissue. More recently, however there has developed an awareness in the art that the normal functioning of the sigmoid valve requires not only the three leaflets but also the three sinuses of Valsalva. In fact, it is now understood that the physiological sigmoid valve is a complex which includes the ventricular outflow tract, valve annulus, leaflets and sinuses of Valsalva with their distal limit of the supraaortic ridge or sino-tubular junction. Because of this awareness, more recently human and animal replacement valves are transplanted as a complete root, i.e. the whole aortic or pulmonary root of the patient is resected and replaced with a cylinder of the donor's homologous or heterologous tissue carrying the sigmoid valve. Both extremities of this natural replacement valved conduit are sutured to the remnant of the patient's tissues (see Kouchoukos N. T. *New Eng J. Med.* 1994;330:1). However, in this operation the correct sizing of the conduit in terms of diameter, length and orientation when suturing it, are essential if valve insufficiency is to be avoided. Distortions from the required dimensions and configuration not only can result in an immediate valve regurgitation but also in a progressive and slow deterioration of the transplanted valve which is subjected to deformation stresses. Because of the foregoing technical difficulties the use of these unsupported valves has not been universally accepted, and therefore many cardiac surgeons still primarily use mechanical or bioprosthetic devices for aortic valve replacement. The present design of an external support for a constructed or manufactured valved conduit, or for homologous or heterologous aortic or pulmonary tissue roots simplifies the surgical technique of their implantation and avoids distortions both at the time of its surgical implantation and during and after chest closure in the very precise geometry of the sigmoid valve complex.

SUMMARY OF THE INVENTION

It is an object of the present invention to provide an external support or frame, which can be sutured to the exterior of a valved conduit or sigmoid valve root and which maintains the geometry of the valved conduit or valve root, particularly during its surgical implantation.

A support frame or stent which meets the foregoing objective is made from a biocompatible solid, single piece of metal or plastic, biocompatible wire or biocompatible soluble or reabsorbable polymers that temporarily maintain their general geometry or configuration. The stent or support frame has a generally cylindrical shape, with ends which are circular when viewed from above and below. From a side view however, both upper and lower ends of the cylinder present three convex curvatures joined at equidistant points at the upper and lower circumference. These upper and lower curves are joined by three vertical struts so that three large saddle shaped paraboloid gaps are formed on the sides of the cylinder. The thickness of the stent although variable according to the material used in its construction, is of only a few millimeters and rounded off so as to avoid sharp angles or edges that might damage tissues. The ultimate shape is that of a wire-like structure which follows substantially perfectly the anatomical shape of the "sinuses of Valsalva" i.e. the line of implantation of the three sigmoid cusps below the stent or frame and the curved line of the sino-tubular junction or supraaortic ridge above the stent. The vertical struts of the stent or frame correspond to the three commissural areas of the natural implanted or fabricated sigmoid valve. The stent of the invention does not come into contact with the circulating blood and therefore does not need to be covered with biocompatible cloth. Different sizes of supports are required to adapt to the different sizes of conduits, that is, for implantation in different patients. After the frame or stent is correctly sutured to the exterior of a valved conduit or sigmoid valve root, the three bulges corresponding to the sinuses of Valsalva protrude through the gaps in the frame.

The support frame or stent of the present invention is completely different from any other valve stent of the prior art because of its function, general shape, and also because in contrast to all previously described stents, it is placed outside the valved conduit (i.e. extravascular) and does not come into contact with circulating blood.

Another object of the present invention is to provide a valved conduit which is used in conjunction with the above-summarized stent or support frame and can be surgically implanted to replace a resected sigmoid valve root.

The foregoing objective is attained by a conduit made from biocompatible membranes or biological tissues obtained from animal or human donors, which in its interior has a trileaflet sigmoid valve formed of the same material. In one preferred embodiment the conduit and trileaflet sigmoid valve is made from pericardium, either from animal or human donors or even from the patient's own pericardium (autologous). The support frame or stent is affixed to the exterior of this valved conduit to ensure that the geometry of the sigmoid valve is maintained during the surgical procedure of implantation and thereafter.

In another aspect the present invention comprises the process of forming the valved conduit from a biological membrane, such as pericardium, fashioned over a template and treated with a cross-linking agent, so as to convert a flat sheet into a tube with three bulges corresponding to what is known as the sinuses of Valsalva. In the interior of the tube three cusps made of the same material are attached to the lower rims of the sinuses of Valsalva of the conduit. In order to insert the appropriate conduit to each patient, a conduit of appropriate size must be constructed. Construction of the valved conduit can be done either in the operating room when autologous tissue is used, or under appropriate clean or sterile conditions when non-autologous (xenogeneic such as porcine, equine or bovine) or allogenic (human) pericardium is used.

The objects and features of the present invention are set forth in the appended claims. The present invention may be best understood, together with further objects and advantages, by reference to the following description, taken in connection with the accompanying drawings.

DESCRIPTION OF THE PREFERRED EMBODIMENTS

The following specification taken in conjunction with the drawings, sets forth the preferred embodiments of the present invention. The embodiments of the invention disclosed herein are the best modes contemplated by the inventor for carrying out his invention in a commercial environment although it should be understood that various modifications can be accomplished within the parameters of the present invention.

Referring now to FIGS. 1a–1e of the appended drawing figures, the preferred embodiment of the external frame or stent 20 of the present invention is disclosed. It should be noted at the outset that although the ensuing description is primarily directed to the use of the frame or stent 20 as an external support for a valved conduit fabricated of biological material, the invention is not so limited. Rather the external frame or stent 20 can also be applied to support natural aortic and pulmonary roots of human or animal origin.

Figure 1A:
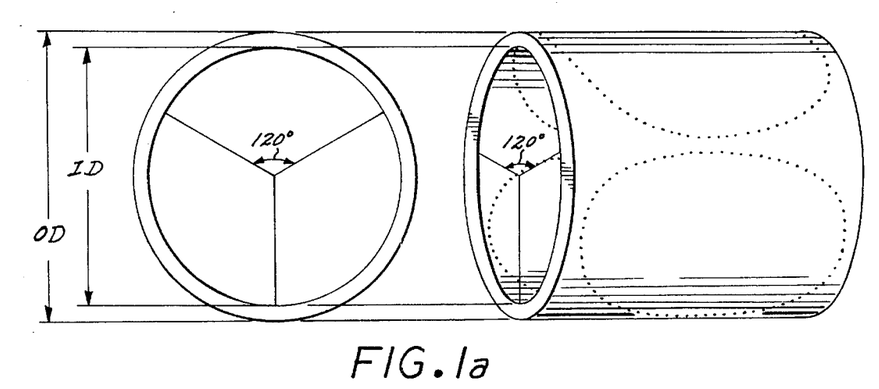
FIG. 1a through 1e are schematic views showing, in a geometrical sense, the formation of a preferred embodiment of the stent or support frame of the present invention, with FIG. 1e showing the actual stent in perspective view.
Figure 1B:
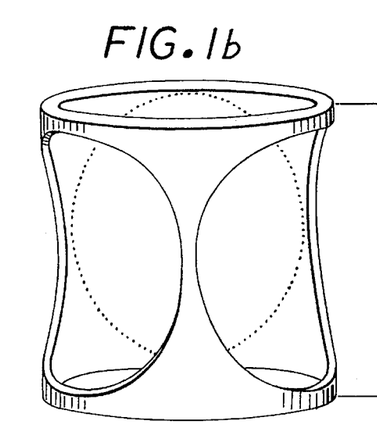
Figure 1C:
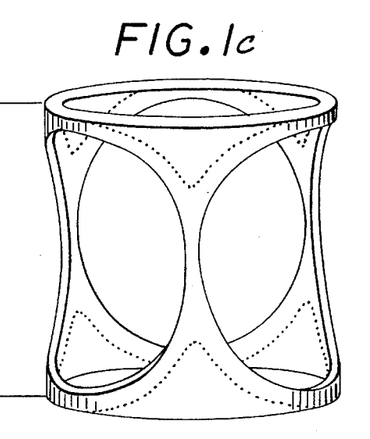
Figure 1D:
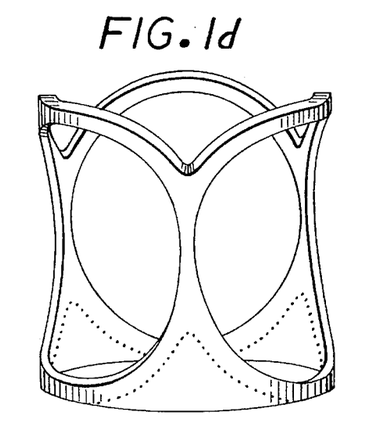
Figure 1E:
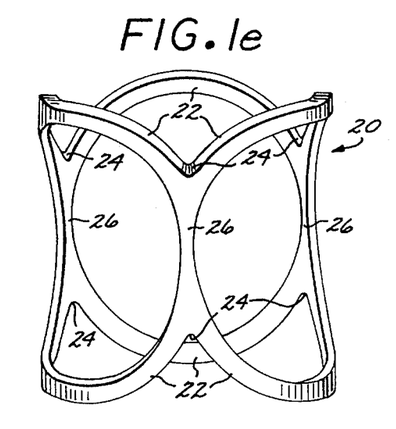

Referring now to FIG. 1e, an important feature of the present invention is the configuration or shape of the frame 20. Specifically, the novel frame 20 of the invention has a shape or configuration adapted to follow the external contours of the normal sinuses of Valsalva (not shown) which are limited below by the line of insertion of the sigmoid valve leaflets, and above to follow the curved supraaortic ridge or sino-tubular junction. The stent 20 can be constructed from several known biocompatible materials which have sufficient rigidity. Such materials include biocompatible metals, including titanium and titanium alloys, and biocompatible non-reabsorbable plastics which are well known in the art. Other alternative materials include biocompatible soluble or reabsorbable polymers such as gelatin and polylactic or polyglycolic acid. As is well known in the art, the latter materials are reabsorbed by the body after implantation within the course of days to several months, depending on the nature of the material. In this regard it is emphasized that the permanent presence of the frame or stent 20 of the present invention is not required for the satisfactory function of the implanted "fabricated" valved conduit or natural autologous, homologous or heterologous sigmoid valve root. The function of the frame or stent 20 is only to maintain the desired geometry of the valved conduit or valve root, thus avoiding distortions occurring at the time of their surgical insertion or soon thereafter.

The stent 20 of the herein described preferred embodiment is constructed from a single solid piece of biocompatible plastic. A preferred plastic is Delrin normally used for human implantation and well known in the prior art. This material has very good properties for the purposes of this invention because of its strength, ease of handling and proven biocompatibility. However, it should be noted that because of their greater strength metal alloy stents in accordance with the present invention can be made of lesser thickness than Delrin or like plastic stents. On the other hand, due to their lesser structural strength, stents of reabsorbable biocompatible material would probably need to be thicker than the herein described Delrin stent 20. The actual cross sectional shape of the material forming the frame 20 can vary according to the type and characteristics of material used for its construction. It can be circular i.e. wire-like, or roughly rectangular i.e. presenting a flat surface on its inside and outside (as in FIG. 1). The edges, however, should be sufficiently rounded to avoid sharpness. FIGS. 1a through 1d illustrate schematically how the preferred embodiment of the stent 20 is shaped into the desired configuration, starting with a cylindrical piece of biocompatible plastic (preferably Delrin) material. It should be noted in this regard that FIGS. 1a through 1d do not necessarily illustrate the process of fabricating the preferred stent 20, rather these figures illustrate how the configuration of the stent 20 is derived from a cylindrical plastic, and thereby clearly illustrate the stent 20 itself.

As it will be apparent, to those skilled in the plastic manufacturing and related arts, the stent 20 can be made by various known methods of manufacture of plastic articles, and can also be made by a technique of fabrication which involves removing or cutting out excess material from a plastic cylinder (tube) substantially as outlined in FIGS. 1a through 1d. Referring now again to these figures, the frame or stent 20 has a circular appearance when it is viewed from the top or bottom. The diameter of the circle on the top and on the bottom is approximately the same, and therefore the stent 20 in this sense has the configuration of a cylinder. In a side view however, each end of the frame has a sinusoidal appearance, having three convex curves 22 of approximately equal length that join at equidistant points 24 of the upper and lower circumferences. These upper and lower joining points 24 are connected to each other by short vertical struts 26. The overall shape of the resulting frame or stent 20 is an open cage with three rounded upper and lower convolutions that encompass three saddle shaped substantially paraboloid spaces. In fact, the configuration of the stent 20 closely corresponds to the anatomical collagenous thickening present in a normal sigmoid valve complex.

Proportions between the height and width of the frame can be varied, for as long as the frame meets its stated objective to externally support a manufactured valved conduit or a natural aortic or pulmonary root. Because of the different sizes of the hearts of different individuals, particularly according to their age, different size frames are required. An approximate range of such sizes, as determined by the internal diameter (i.d.) of the lower or in-flow circumference, is between 15 and 30 mm. As is illustrated in FIGS. 1b and 1c, the height of the stent 20 approximately equals its outer diameter. The outer diameter, of course, depends on the thickness of the wall as well. In the specific example illustrated in FIGS. 1a through 1e the wall thickness is approximately 1 mm; further in this specific example the internal diameter is 18 mm, and the cut-outs to form the paraboloid spaces are of 18 mm diameter. The following Table 1, illustrates the dimensions of further examples of the preferred embodiment of the stent 20 (made from Delrin of 1 mm wall thickness.)

TABLE 1

| O.D. | i.d. | height | cut-outs |
|------|------|--------|----------|
| 15   | 13   | 15     | 13       |
| 21   | 19   | 21     | 19       |
| 25   | 23   | 25     | 23       |
| 29   | 27   | 29     | 27       |

As it was mentioned above, and is described further below, the external frame or stent 20 of the invention is sutured on the exterior of a fabricated valved conduit to simplify the surgical implantation of the valved conduit and ensure its correct alignment when replacing a diseased or congenitally deformed outflow tract between the right ventricle and the pulmonary artery. The same stent or support frame can be sutured on the external or adventitial aspect of an aortic or pulmonary root, whether of autologous, homologous or heterologous in origin.

Referring now to FIGS. 2–11, a valved conduit 28 of the present invention and the process of fabricating the same from biological tissues such as pericardium, pleura, peritoneum and duramater, or from biocompatible synthetic membranes, is illustrated. The biocompatible biological tissue can be of human (allogeneic) or animal (xenogenic) origin, and if human it may be from the patient's own tissues (autograft) or from a cadaver (homograft). An example of suitable biocompatible synthetic membrane is "expanded" polytetrafluoroethylene (GoreTex).

Figures 2A, 2B, 3A:
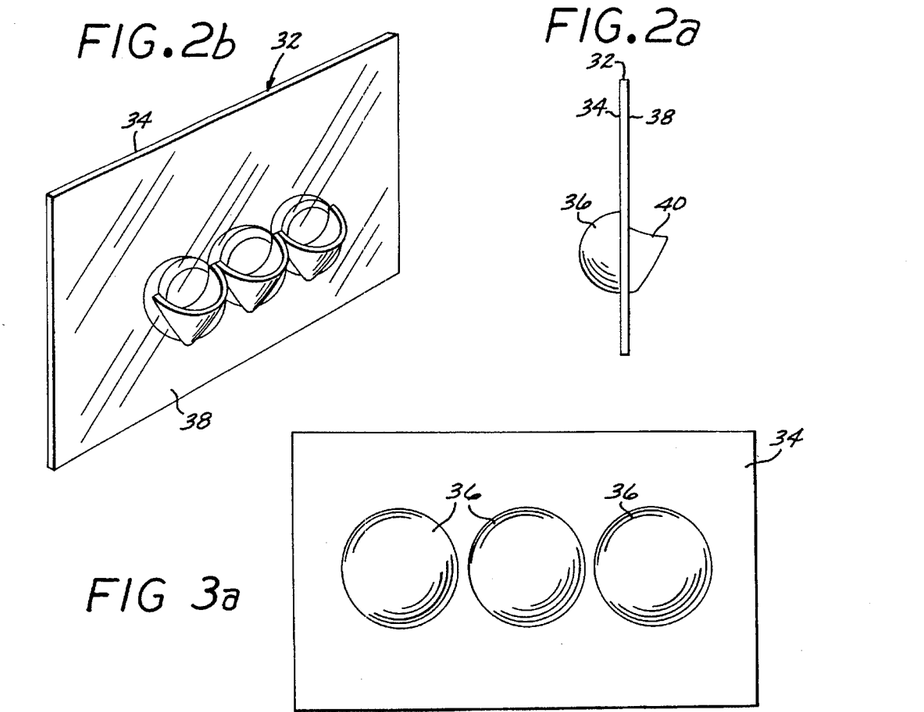
FIG. 2a is a lateral end view of the template used to construct a valved conduit of the invention from a flat sheet of biocompatible membrane or biological tissue and FIG. 2b is a perspective view of the same.
FIGS. 3a–3c are respectively outer, inner and lateral views of the template of FIG. 2, showing the dimensions of the same related to the valved conduit or sigmoid root diameter.

The preferred embodiment of the valved conduit for either reconstruction of the right ventricular outflow tract or to bridge it completely, comprises pericardium (membrane of the pericardial sac), and the following description of the valved conduit 28 and its fabrication is directed to this preferred embodiment. Thus, a rectangular piece of pericardium 30 is resected and cleaned by gentle dissection from the adipose tissue and fibrous strands present on the mediastinal or outer surface of the membrane. An appropriate template 32, as shown in FIG. 2a and 2b, is selected on the basis of the desired size of the conduit 28 to be fabricated.

Figure 3B:
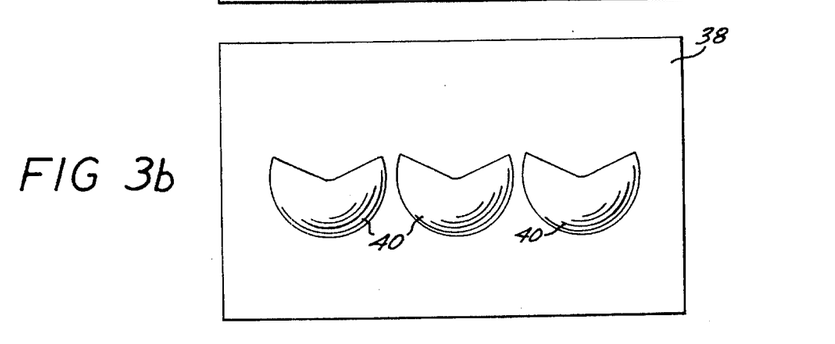
Figure 3C:
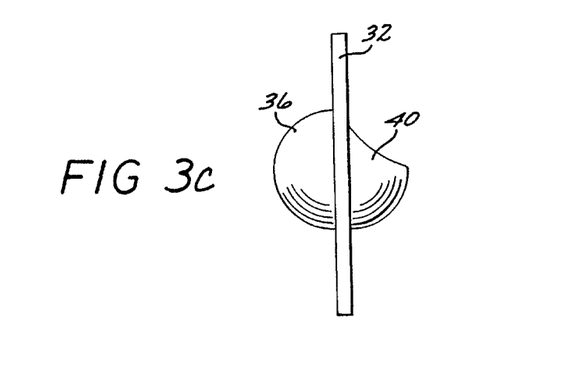

The template 32 which is made of plastic or metal, comprises a flat, rectangular plate 32 of a few millimeters thickness. On one of its surfaces 34 there are three hemispheres 36 placed contiguously. These hemispheres 36 have a diameter appropriate to the future size of the conduit 28 and correspond to the shape and size of the sinuses of Valsalva of the conduit, i.e. of the patient for whom the valved conduit 28 is fabricated. During the fabrication process the side or surface 34 with the hemispheres 36 becomes the exterior or outer surface of the valved conduit 28. The other side or inner surface 38 of the template 32 has three roughly circular but truncated protrusions 40 placed in continuity and situated to match, as exactly as possible, the position of the three hemispheres 36. The truncated protrusions 40 form a positive mold for the three sigmoid leaflets which are to be formed within the conduit 28. Dimensions of the template 32 of the invention relative to the diameter of the valved conduit 28 (valve annulus taken as the unit) are shown in FIGS. 3a–3c. In FIG. 3a the "outer template view" corresponds to the outer surface 34 of the template 32 shown in FIGS. 2a and 2b. In FIG. 3b the "inner template view" corresponds to the inner surface 38 of the template shown in FIG. 2a.

Figure 4:
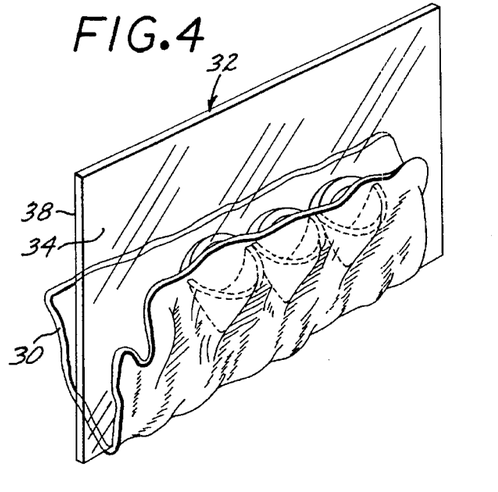
FIG. 4 is a perspective view showing the placement of a flat sheet of biological membrane over the template in order to shape it into the appropriate form in accordance with the present invention.

Referring now to FIG. 4, the rectangular piece of pericardium 30 is folded over the template 32 so that it covers both outer and inner surfaces 38 and 34 of the template 32 and fits snugly its hemispherical 36 and truncated 40 protrusions. In this step of the fabrication process care must be taken so that the smooth (mesothelial) surface of the pericardium 30 faces the template 32. This way the smooth (mesothelial) surface of the pericardium faces the interior of the conduit 28 and the outflow or arterial aspect of the valve leaflets. The pericardium 30 held on to the template 32 with strings (not shown) or rubber bands (not shown), is then immersed in a cross-linking solution (not shown). In accordance with the present preferred embodiment the cross-linking solution is a medical grade buffered glutaraldehyde solution of low concentration. When autologous pericardium is used, the immersion time is very short, in the order of a few minutes, while for non-autologous tissue a longer immersion time is required. The technique of cross-linking per se is well known in the prior art and can be practiced with other known chemical or physical tissue tanning solutions and methods.

Figure 5A:
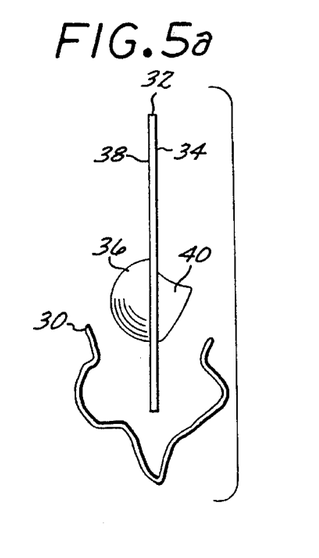
FIG. 5a is a schematic lateral view showing a step of removing the shaped biological membrane from the template; and 5b and 5c are perspective and schematic side views showing a step of suturing the biological membrane in the process of forming a valved conduit.
Figures 5B, 5C:
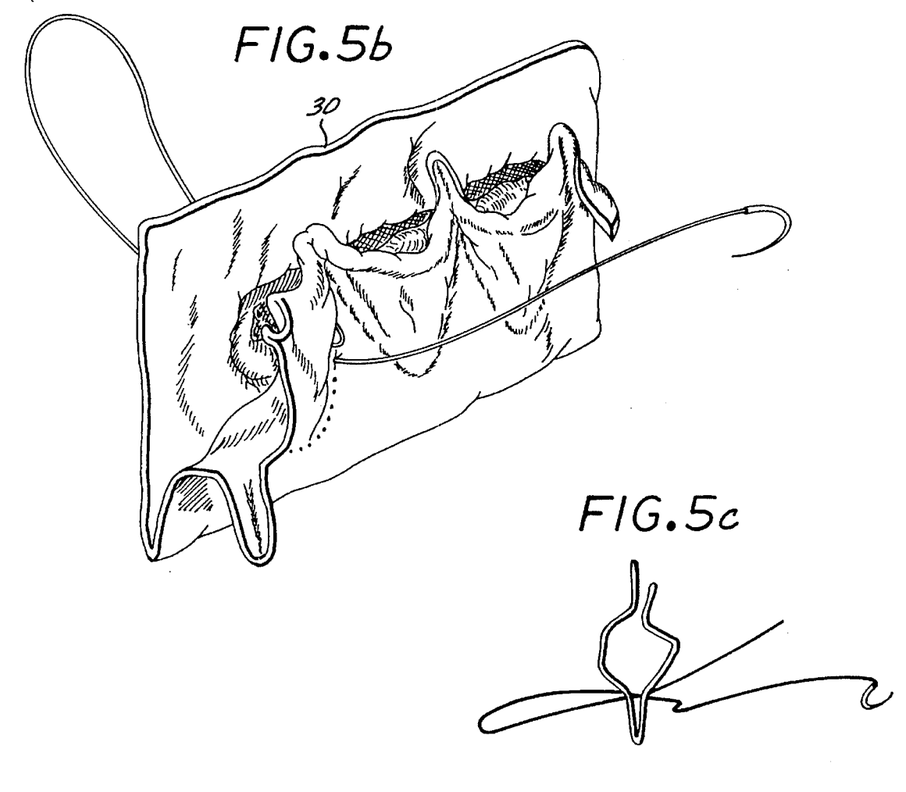
Figure 6:
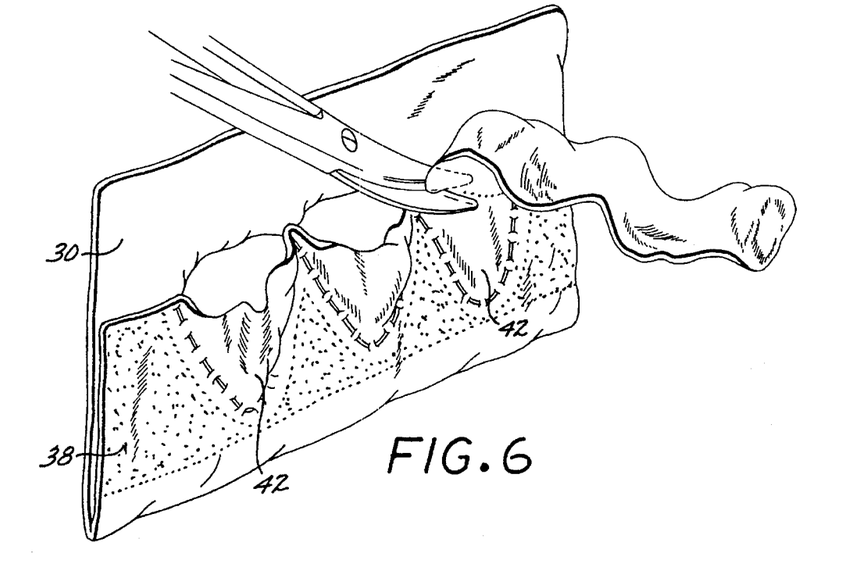
FIG. 6 is a perspective view showing the step of resecting excess tissue on the inner side of the folded membrane which becomes the interior of the valved conduit of the invention.
Figure 7:
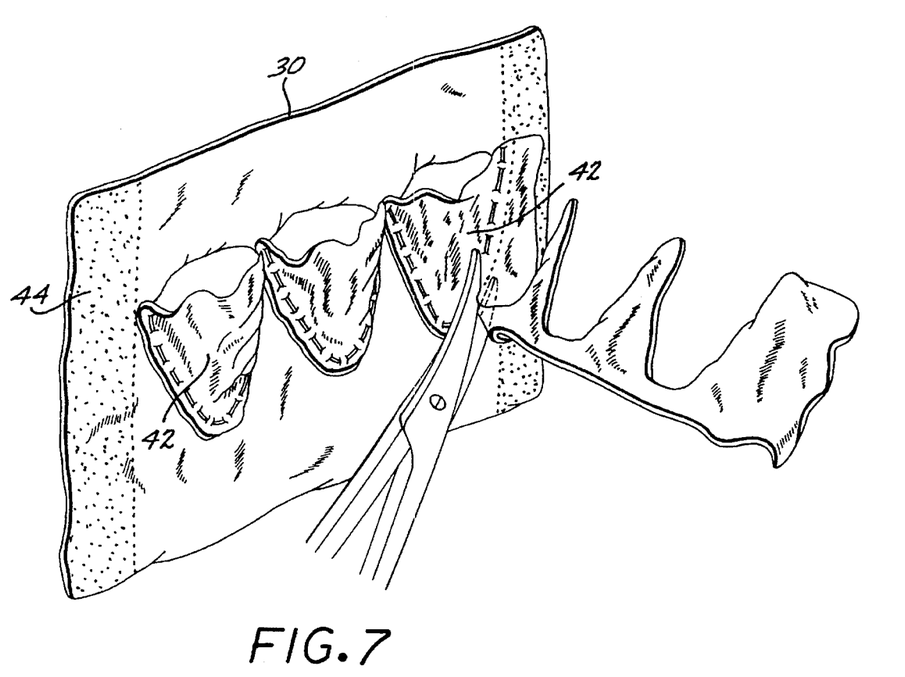
FIG. 7 is a perspective view showing a further step of resecting excess tissue on the side of the folded membrane which becomes the interior of the valved conduit of the invention.
Figure 8:
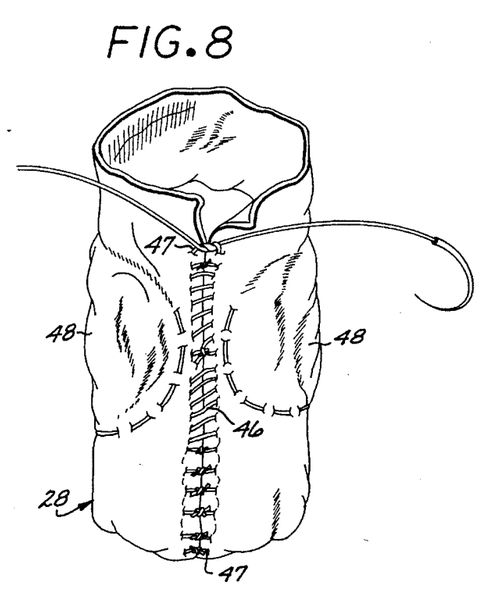
FIG. 8 is a perspective view showing the step of suturing the membrane which had been folded into a tubular form and which forms the valved conduit of the invention.

Referring now to FIG. 5, after cross-linking or fixation, the folded pericardium membrane 30 is separated from the template 32, as is schematically shown in FIG. 5a. The two folded parts are then joined with a continuous surgical suture that follows the contours of the three hemispheric and truncated protrusions 35 and 40, as shown in FIGS. 5b and 5c. Referring now to FIG. 6, excess tissue on the inner side 38 of the pericardium membrane 30 is cut away so that three generally round leaflets 42 result. The edges shown as being cut on FIG. 6 correspond to the free edges of the newly constructed valve leaflets. FIG. 7 shows that thereafter the membrane 30 is trimmed by excising its redundant portions 44 shown as a dotted area in the figure, so that when the membrane 30 is folded into the shape of a tube the lateral aspects of the two lateral leaflets 42 come into contact and the three bulges 48 corresponding to the sinus of the Valsalva, protrude exteriorly. As is shown in FIG. 8, the lateral edges of the membrane 30 are then sutured together with a continuous surgical suture 46. In order to allow the surgeon (not shown) to adapt the length of the valved conduit 28 to the individual patient (not shown), suturing is started at the center, i.e. where the sinus of Valsalva bulges 48 are closest to one another, and continuous suturing is stopped at the level where the bulges 48 terminate, i.e. corresponding with the supraaortic ridge above and the line of insertion of the leaflets below. The remaining of the suturing of the conduit 28 is done with interrupted surgical sutures 47 so that if the surgeon (not shown) decides to shorten the conduit 28 by sectioning off an upper or lower segment, the continuous suture is not broken with the ensuing disruption of the conduit 28.

Figure 9:
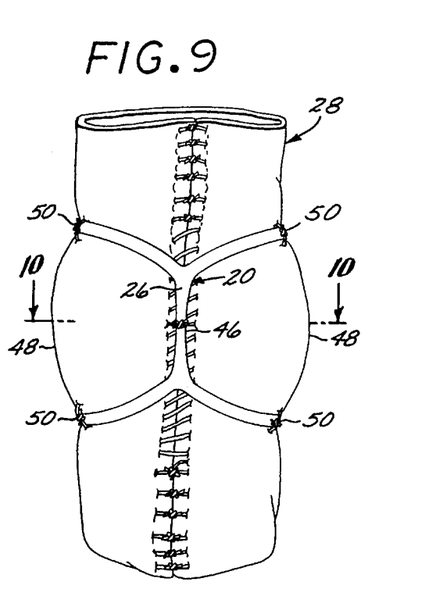
FIG. 9 is a perspective view of the combination of the valved conduit with the external support or frame affixed thereto in accordance with the present invention.

Referring now to FIG. 9, the valved conduit 28 which has been constructed in the manner described above, is then inserted inside the appropriately dimensioned support frame or stent 20. Appropriate matching dimensions in this regard require the frame or stent 20 to fit snugly over the conduit 28 and this occurs when the internal diameter of the stent 20 is about 1–2 mm larger than the diameter of the conduit 28. As is shown on FIG. 9 the frame or stent 20 is placed so that it fits exactly with the bulges or sinuses of Valsalva 48 of the conduit 28 which protrude through the saddle shaped lateral apertures of the frame 20. When the frame 20 is properly placed the vertical struts 26 must coincide externally with the internally placed commissures or contact area of the three new leaflets 42. Once properly situated the frame or stent 20 is held in position by several surgical stitches 50 passed through the pericardium 30 and around the stent 20, as shown in FIG. 9.

Figures 10, 11:
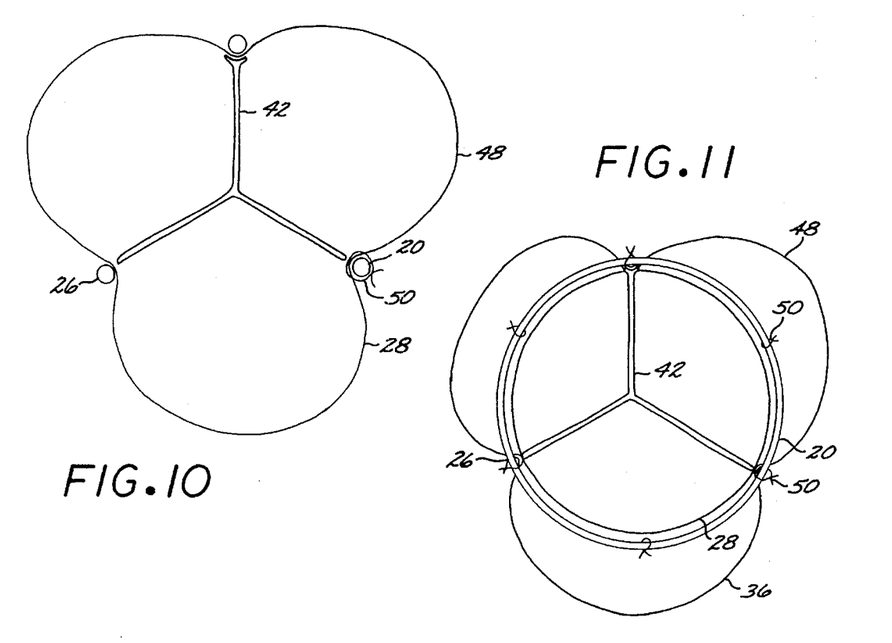
FIG. 10 is a schematic cross-sectional view, taken on lines 10,10 of FIG. 9, showing the valve leaflets disposed within the interior of the valved conduit.
FIG. 11 is an end view of the combination of FIG. 9, showing the valve leaflets disposed within the interior of the valved conduit.

FIGS. 10 and 11 illustrate diagramatically the valve leaflets 42 within the interior of the valved conduit 28.

The external frame or stent 20 can also be used as a support during surgical implantation and thereafter of a natural aortic or pulmonary root. In this case the donor human or animal root (not shown) is dissected from the donor heart (not shown) so that a cylinder results with an inflow or lower orifice corresponding to the outflow tract of the ventricle and an outflow or upper orifice corresponding to the arterial aspect. This outflow orifice should be situated a few millimeters beyond the sino-tubular junction. This cylinder therefore contains all the anatomical parts of the sigmoid valve complex i.e. the fibro-muscular ventricular outflow, the three valve leaflets and the complete three sinuses of Valsalva. An external frame or stent 20 of the appropriate size is selected and placed outside the root (not shown). The inflow or lower part of the frame 20 should be disposed exactly at the level of the insertion of the three leaflets, the vertical struts 26 at the respective locations of the three commissures and the upper or outflow orifice of the frame should be fitted to the supraaortic ridges. The three sinuses of Valsalva of the root should protrude freely through the lateral orifices of the frame 20. Once properly placed the frame 20 is held in position on the donor root, by surgical sutures. The final prepared root should have a few millimeters of tissue beyond the frame at both its upper and lower orifices so that it can be sutured to the patient's remaining tissues.

Several modifications of the above described novel valved conduit and external supporting frame and of the associated parts and processes may become readily apparent to those skilled in the art in light of the above disclosure. Therefore, the scope of the present invention should be interpreted solely from the following claims, as such claims are read in light of the disclosure.

What is claimed is:

1. A frame to be used to support a sigmoid valved conduit during surgical implantation and thereafter, and to be affixed to the exterior of the valved conduit, the frame essentially consisting of biocompatible plastics or metals, and having the configuration of an open cage which is substantially circular when viewed from the top and the bottom, and having a side view which is that of a cylinder open in its top and bottom and is formed on its top of three convex curvatures which are joined at equidistant points at the upper circumference of said cylinder, and on its bottom of three convex curvatures which are joined at equidistant points at the bottom circumference of said cylinder, the equidistant joining points of said top and bottom curvatures being connected to one another by three substantially vertically disposed struts, whereby three lateral saddle-shaped substantially paraboloid openings are formed in the cage.

2. The frame of claim 1 wherein the material of the frame is biocompatible metal.

3. The frame of claim 1 wherein the material of the frame is biocompatible plastic.

4. The frame of claim 1 wherein the material of the frame is biocompatible reabsorbable or soluble polymer.

5. The frame of claim 1 dimensioned to be placed on the outside (adventitial) surface of a human aortic valve root to be held by sutures so that the sinuses of Valsava protrude through the side openings of the frame.

6. The frame of claim 1 dimensioned to be placed on the outside (adventitial) surface of a human pulmonary valve root so that the sinuses of Valsava protrude through the side openings of the frame.

7. The frame of claim 1 dimensioned to be placed on the outside (adventitial) surface of an animal aortic valve root so that the sinuses of Valsalva protrude through the side openings of the frame.

8. The frame of claim 1 dimensioned to be placed on the outside (adventitial) surface of an animal pulmonary valve root so that the sinuses of Valsava protrude through the side openings of the frame.

9. A prosthetic sigmoid valve complex to be used for surgical implantation to replace a resected native sigmoid valve complex, comprising in combination:

a valved conduit comprising biological tissue or biocompatible synthetic membrane, having the configuration of a tube having three bulges in its exterior, said bulges conforming to the shape of the sinuses of Valsalva of the human heart and having a trileaflet valve in its interior;

a frame affixed to the exterior of the valved conduit, the frame consisting of material selected from biocompatible plastics and metals, and having the configuration of an open cage which is substantially circular when viewed from the top and the bottom, and having a side view which is that of a cylinder open in its top and bottom and is formed on its top of three convex curvatures which are joined at equidistant points at the upper circumference of said cylinder, and on its bottom of three convex curvatures which are joined at equidistant points at the lower circumference of said cylinder, the equidistant joining points of said top and bottom curvatures being connected to one another by three substantially vertically disposed struts, whereby three lateral saddle-shaped substantially paraboloid openings are formed in the cage, the frame being affixed on the exterior of the valved conduit in a position wherein the bulges conforming to the shape of the sinuses of Valsalva are disposed within the paraboloid openings of the cage, and the vertical struts are aligned with commissures formed in the valve leaflet within the interior of the conduit.

10. The sigmoid valve complex of claim 9 wherein the valved conduit consists essentially of biological tissue and surgical stitching and wherein the valve in the interior of the valved conduit is formed of three leaflets disposed in the interior of the conduit.

11. The sigmoid valve complex of claim 10 wherein the valved conduit is formed of autologous pericardium tissue.

12. The sigmoid valve complex of claim 10 wherein the valved conduit is formed of homologous pericardium tissue.

13. The sigmoid valve complex of claim 10 wherein the valved conduit is formed of heterologous pericardium tissue.

14. The sigmoid valve complex of claim 10 wherein the valved conduit is formed of synthetic membrane.

15. The sigmoid valve complex of claim 9 wherein the material of the frame is biocompatible metal.

16. The sigmoid valve complex of claim 9 wherein the material of the frame is biocompatible plastic.

17. The sigmoid valve complex of claim 9 wherein the material of the frame is biocompatible reabsorbable or soluble polymers.

* * * * *